United States Patent [19]

Fayter, Jr. et al.

[11] 4,446,077
[45] May 1, 1984

[54] SUBSTITUTED-CYCLOPROPYL SULFONES
[75] Inventors: Richard G. Fayter, Jr., Fairfield; Allen L. Hall, Amelia, both of Ohio
[73] Assignee: National Distillers and Chemical Corporation, New York, N.Y.
[21] Appl. No.: 345,875
[22] Filed: Feb. 4, 1982
[51] Int. Cl.$^3$ .................. C07C 121/48; C07C 121/66
[52] U.S. Cl. ................................... 260/465 K; 71/88; 71/103; 424/278; 424/306; 549/501; 260/464; 260/465 D; 560/11; 560/124; 562/429; 562/506; 564/162; 564/190
[58] Field of Search ........................... 260/464, 465 K
[56] References Cited
U.S. PATENT DOCUMENTS
3,047,611 7/1962 Moore et al. ....................... 560/124
4,252,739 2/1981 Fayter, Jr. et al. ............. 260/454 X OTHER PUBLICATIONS
Genet, et al.; J. Org. Chem., (1981), 46, pp. 2414–2417.
Cho, et al.; J. of Polymer Science. Polymer Letters Edition., vol. 18; pp. 639–642, (1980).
Cho, et al.; J. of Polymer Sciences. Polymer Chemistry Edition, vol. 18; pp. 3053–3057, (1980).
Dehmlow, Angew Chem. Internat. Edit., vol. 13, pp. 170–179, (1974).

Primary Examiner—Joseph Paul Brust
Attorney, Agent, or Firm—Kenneth D. Tremain; Gerald A. Baracka

[57] ABSTRACT

Novel 2-vinyl- and 2-ethyl-cyclopropyl sulfones are provided. In addition to the ethyl or vinyl group at the 2-position of the ring, the compounds of this invention are disubstituted at the 1-position with a sulfonyl group and an acyl, nitrile or nitrile-derived radical. The sulfones of this invention are useful chemical intermediates from which a wide variety of pesticidal, herbicidal or biologically active compounds can be prepared and are useful monomers for anionic or radical polymerizations.

2 Claims, No Drawings

SUBSTITUTED-CYCLOPROPYL SULFONES

BACKGROUND OF THE INVENTION

1. Field of the Invention

The present invention is directed to novel substituted-cyclopropyl sulfones. More specifically, in addition to having a sulfonyl

group on the ring, the compounds of this invention have a vinyl or ethyl group substituted in the 2-position and an acyl moiety or nitrile or radical derived therefrom present with the sulfonyl group in the 1-position. The sulfones of this invention are useful chemical intermediates and undergo anionic or radical polymerizations.

2. Discussion of the Prior Art

The polymerization of 1,1-disubstituted 2-vinylcyclopropanes has been documented by Iwhan Cho and co-workers (see *Journal of Polymer Science*, Vol. 17, 3169–3182(1979); Vol. 17, 3183–3191(1979); Vol. 18, 3053–3057(1980); and Polymer Letters Edition, Vol. 18(9), 639–42(1980)). In addition to radical initiated 1,5-type polymerizations, it was also observed that anionic polymerization can be accomplished with such compounds via ring-opening and without participation of the vinyl group. It is thus possible to achieve reactive polymeric materials having a vinyl group and nitrile or ester moiety pendant to the polymer chain.

In view of the desirable properties generally attributed to the presence of sulfonyl groups in polymeric materials, it would be highly desirable and advantageous to have a reactive cyclopropyl monomer bearing such substituents which could be readily polymerized under anionic or radical conditions in accordance with the prior art teachings. However, the preparation of such compounds has heretofore not been possible in view of the limitations of the condensation procedures typically used to prepare cyclopropane derivatives. While E. V. Dehmlow report the preparation of a cyclopropane compound having a sulfonyl group substituted thereon via a carbene insertion reaction (*Angew Chem. Internat. Edit.*, Vol. 13, No. 3, 170–179(1974)), the reaction is not suitable for the preparation of vinyl substituted cyclopropane sulfones.

SUMMARY OF THE INVENTION

We have now quite unexpectedly discovered substituted-cyclopropyl sulfones useful as chemical intermediates and reactive monomers. The novel substituted-cyclopropyl sulfones are prepared using the phase-transfer process of U.S. Pat. No. 4,252,739 and are disubstituted at the 1-position of the ring and have a vinyl or ethyl group in the 2-position.

The compounds of this invention correspond to the formula

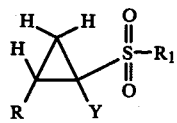

where R represents an ethyl or vinyl group, $R_1$ represents a hydrocarbon radical of from 1 to 30 carbon atoms, and Y is an acyl radical, nitrile or nitrile-derived radical, such as an amine, quaternary amine, amide or carboxylate. Preferably $R_1$ will be an aliphatic, cycloaliphatic or aromatic moiety having from 1 to 20 carbon atoms. Particularly preferred acyl moieties correspond to the formula

where $R_2$ is a hydrocarbon radical as defined for $R_1$.

Especially useful cyclopropane compounds have the formulae

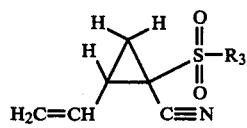

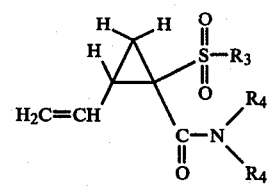

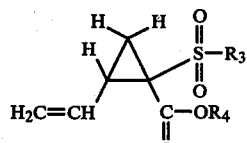

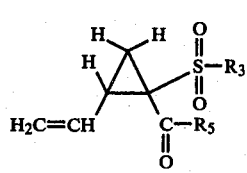

where $R_3$ and $R_5$ are, independently, $C_{1-8}$ alkyl, $C_{3-8}$ alkenyl, cyclohexyl, phenyl, benzyl or $C_{1-4}$ alkyl-substituted cyclohexyl, phenyl or benzyl and $R_4$ is hydrogen or a radical as defined for $R_3$ and $R_5$.

DETAILED DESCRIPTION

The novel substituted-cyclopropyl sulfones of this invention have the general formula

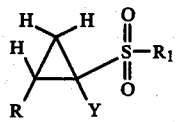

where R is an ethyl or vinyl group, $R_1$ is a hydrocarbon radical having from 1 to 30 carbon atoms, and Y is an acyl group, nitrile or nitrile-derived radical. Whereas the formula does not take into account the various isomeric forms of these compounds which can exist, i.e., geometric and stereo isomers and mixtures and racemates thereof, all such products are within the scope of this invention.

The hydrocarbon radical $R_1$ can contain from 1 up to 30 carbon atoms and may be aliphatic, cycloaliphatic, aromatic or a combination of such moieties. When $R_1$ is an alkyl group, i.e., an aliphatic hydrocarbon radical, it will contain from 1 to 30 and, more preferably, 1 to 20 carbon atoms and may be straight-chain or branched, saturated or unsaturated. Radicals which contain unsaturation generally have no more than one double bond for every four carbon atoms.

Cycloaliphatic hydrocarbon radicals from which $R_1$ may be selected are saturated or unsaturated and can contain one or more hydrocarbon substituents on the ring. The cycloaliphatic radicals will have from 3 to 30 carbon atoms, however, preferred cycloaliphatic radicals contain from 5 to 20 carbon atoms and correspond to the formula

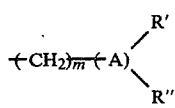

where m is an integer from 0 to 8 and, more preferably, 0 to 4, A represents a non-aromatic 5- or 6-membered carbon ring system, and $R'$ and $R''$ are hydrogen, a $C_{1-8}$ alkyl or alkenyl group, phenyl or benzyl. Particularly advantageous cycloaliphatic radicals of the above type are those wherein the

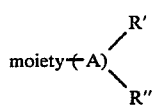

is an unsubstituted or mono- $C_{1-8}$ alkyl- or alkenyl-substituted cyclopentyl, cyclopentenyl, cyclohexyl, cyclohexenyl or cyclohexa-2,4-dienyl group.

When $R_1$ is an aromatic hydrocarbon radical, it will contain from 6 up to about 30 carbon atoms and may consist of a single ring or fused-ring system which can be unsubstituted or have one or more hydrocarbon groups substituted thereon. Especially useful aromatic radicals contain from 6 to 20 carbon atoms and correspond to the formula

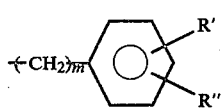

where m is an integer from 0 to 8, and more preferably 0 to 4, and $R'$ and $R''$ are hydrogen, a $C_{1-8}$ alkyl or alkenyl group, phenyl or benzyl. Preferred aromatic radicals include phenyl, $C_{1-8}$ alkyl- or alkenyl-substituted phenyl, benzyl and $C_{1-8}$ alkyl- or alkenyl-substituted benzyl.

When Y is an acyl group, $R_2$ is a hydrocarbon radical of 1 to 30 carbon atoms. $R_2$ can be selected from any of the groups defined above for $R_1$ and can be the same as or different than $R_1$. Preferably, $R_2$ will be a $C_{1-8}$ alkyl, $C_{3-8}$ alkenyl, phenyl, benzyl or $C_{1-4}$ alkyl-substituted phenyl or benzyl. More than one alkyl substituent may be present on the ring and it is also possible to have $C_{1-4}$ alkoxyl groups substituted thereon.

Y can also be nitrile $—C{\equiv}N$ or any radical derived therefrom such as amines, quaternary amines, amides or carboxylates. The hydrogenation of nitriles to produce amines is well known. Also, it is equally well recognized to hydrolyze nitriles to obtain the corresponding amide and/or carboxylic acid, depending on the conditions used and the degree of hydrolysis. From the amine, amide and carboxylic acid groups, it is possible to obtain a variety of other derivatives using established reaction procedures. For example, the carboxyl group can be reacted with alcohols, alkanolamines, poly(oxyalkylene)glycols, monoalkyl ethers of poly(oxyalkylene)glycols, and the like.

By judicious derivatization of the cyclopropyl sulfones in the above manner, it is possible to obtain useful 2-ethyl and 2-vinylcyclopropane compounds having a sulfonyl group and an ester group substituted at the 1-position of the ring and which exhibit biological activity, herbicidal properties or pesticidal properties. Such compounds have the formula

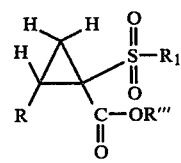

where R and $R_1$ are the same as defined above and $R'''$ is a heteroalkyl or heterocyclic group having from 3 to 20 carbon atoms. Particularly useful heteroalkyl and heterocyclic radicals include:

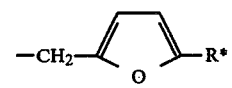

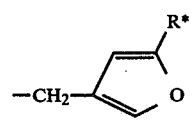

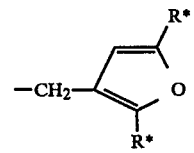

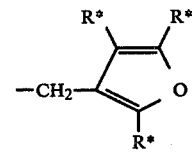

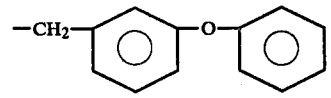

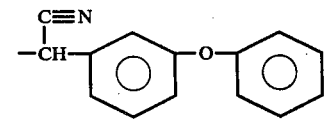

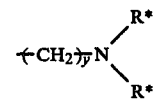

-continued

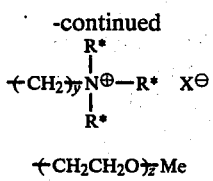

+CH₂CH₂O)ₓMe or

+CH₂CH₂O)ₓEt where R* is a C₁₋₄ alkyl, C₁₋₄ alkenyl, C₁₋₄ hydroxyalkyl, phenyl or benzyl, Me is methyl, Et is ethyl, y is an integer from 2 to 6, z is an integer from 1 to 10 and X represents an anion such as halide, hydroxide, sulfate, nitrate, acetate, alkylsulfate, alkylphosphate, fluoroborate and the like.

Depending on the nature of the ester (R''') group, it is possible to obtain herbicidal compounds capable of modifying plant growth including retardation of growth, defoliation, dessication, regulation, stimulation, dwarfing and, in some cases, killing the plant. In addition to products useful for the treatment of established plants and emerging seedlings, compounds useful as seed coatings are obtainable. Insecticidal compositions useful for the control of beetles, flies, mosquitos, spiders, lice, mites, ticks, nemotodes and other pests can also be produced. Still other compounds which exhibit biological activity can be obtained in this same manner.

To obtain such products, the cyclopropane carboxylic acid, acid halide or lower alkyl ester thereof, is typically utilized. Any process which is non-destructive to the cyclopropane ring can be employed. For example, the cyclopropane carboxylic acid, can be directly reacted with the desired alcohol or alcohol mixture employing conventional esterification procedures and suitable conditions. Alkali salts of the aforementioned acids may also be reacted with suitable active halide compounds to produce the desired cyclopropyl esters. Acid halides of the vinyl- or ethylcyclopropane can also be reacted with the alcohol or corresponding alkali metal alkoxide. The carboxylates can also be obtained by transalcoholysis of a lower alkyl ester, preferably methyl or ethyl, of the cyclopropane carboxylic acid with the desired alcohol or mixture of alcohols. Transalcoholysis of the cyclopropane lower alkyl esters is carried out in accordance with conventional procedures.

By virtue of their reactivity and ability to be polymerized under either anionic or radical conditions, the 2-vinylcyclopropyl sulfones are particularly advantageous. These compounds undergo both 1,2-type polymerization via the vinyl group and 1,5-type polymerization through a ring-opening mechanism. It is possible, utilizing the 2-vinylcyclopropyl sulfones, to obtain polymeric materials having a sulfonyl group pendant to the polymer chain. While the vinylcyclopropyl sulfones can be homopolymerized, primarily the compounds of this invention are utilized to modify the properties of known polymeric materials and are copolymerized in minor amounts with one or more other monomers. Depending on the polymerization conditions, the comonomers, and the particular 2-vinylcyclopropyl sulfone used, polymeric products having widely divergent physical properties can result. Especially useful 2-vinylcyclopropyl sulfones for this purpose include:

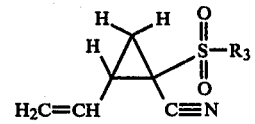

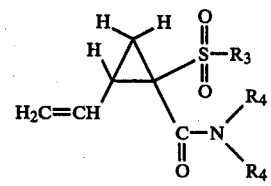

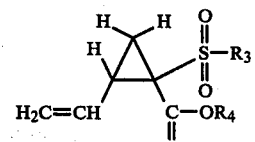

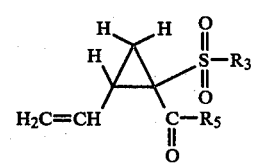

where $R_3$ and $R_5$ are, independently, selected from $C_{1-8}$ alkyl, $C_{3-8}$ alkenyl, cyclohexyl, phenyl, benzyl or $C_{1-4}$ alkyl-substituted cyclohexyl, phenyl and benzyl, and $R_4$ is hydrogen or a radical as defined for $R_3$ and $R_5$.

In addition to the sulfones, sulfoxides corresponding to the above formulae can be obtained in a similar manner following the process of U.S. Pat. No. 4,252,739. Such compounds will have a sulfinyl

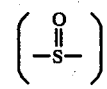

group substituted at the 1-position on the ring. The remaining ring substituents can be the same as described above, i.e. an acyl, nitrile or nitrile-derived group in the 1-position and an ethyl or vinyl group in the 2-position. The sulfinyl groups will be of the same general type as defined for the sulfonyl moieties.

The following examples illustrate more fully the preparation of the novel substituted-cyclopropyl sulfones of this invention. The examples are not intended as a limitation on the scope of the invention. Numerous variations are possible and will be evident to those skilled in the art to which the invention pertains.

EXAMPLE I

1-Phenylsulfonyl-1-cyano-2-vinylcyclopropane was obtained by the phase transfer reaction of phenylsulfonylacetonitrile and 1,4-dichlorobutene-2 in accordance with the procedure of U.S. Pat. No. 4,252,739. For the reaction 22.4 g (0.4 mol) potassium hydroxide and 4.04 g tricaprylylmethylammonium chloride were charged to a glass reactor equipped with a stirrer, thermometer and dropping funnel with 200 cc methylene dichloride. To this mixture was added 36.2 g (0.2 mol) phenylsulfonylacetonitrile (Parish Chemical Co.) while gradually heating to 28° C. with agitation. 1,4-Dichlorobutene-2 (27.5 g, 0.22 mol) was then added dropwise with the application of external cooling at a rate such that the temperature of the reaction mixture did not exceed 31° C. The reaction mixture was maintained with stirring at 28° C. for about 20 hours, filtered and methylene chloride removed under vacuum. The resulting viscous dark brown residue was extracted several times with hot isopropanol and hexane to yield a greenish-yellow solid. By repeated recrystallization of the solid from 95% ethanol/5% methanol, highly pure 1-phenylsulfonyl-1-cyano-2-vinylcyclopropane

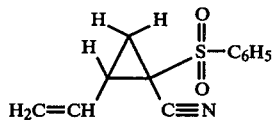

was obtained as white crystals having a short needle-like structure (M.p. 80.0°–80.5° C.). Elemental analysis (C,H and N) of the product agreed with the calculated theoretical values. The structure was also confirmed by mass spectroscopy and nuclear magnetic resonance spectroscopy.

Mass spectrum m/e 233(M+)

nmr (CDCl$_3$) τ 1.75–2.55(5 phenyl H, mult.); 4.00–4.85 (3 vinyl H, mult.); 6.60–7.30 (1H(2 cyclopropyl ring position), b. mult.); 7.65–8.40(2H)3 cyclopropyl ring position), well defined mult.).

Similar results are obtained using methylsulfonylacetonitrile. Also, 1-phenylsulfonyl-1-cyano-2-ethyl-cyclopropane is obtained by carrying out a reduction of the vinyl group using tosyl hydrazine. The reduction of the 1-phenylsulfonyl-1-cyano-2-vinylcyclopropane is accomplished in a suitable solvent medium, such as diglyme.

A polymeric material was produced when 1-phenylsulfonyl-1-cyano-2-vinylcyclopropane was heated with α,α'-azobisisobutyronitrile or benzoyl peroxide at 95° C. Similarly, copolymers are obtained when 1-phenylsulfonyl-1-cyano-2-vinylcyclopropane is combined with acrylonitrile and copolymerized.

EXAMPLE II

In a manner similar to that described in Example I, phenylsulfonyl-acetone was reacted with 1,4-dichlorobutene-2 to prepare 1-phenylsulfonyl-1-acetyl-2-vinylcyclopropane. For the reaction, 9.91 g (0.05 mol) phenylsulfonylacetone (Parish Chemical Co.) and 6.25 g (0.05 mol) 1,4-dichlorobutene-2 were combined in 20 cc sulfolane containing 5 mole percent tricaprylylmethylammonium chloride and crushed 85% potassium hydroxide (6.6 g; 0.10 mol) added in small portions with stirring over a 10 minute period. The reaction mixture was then stirred at 35°–40° C. for about 3½ hours. At the completion of the reaction, 100 cc water was added to dissolve the white granular precipitate which had formed and the mixture extracted several times with ether. A crude red oil (10.8 g) was obtained after removal of the ether. Both the cis and trans isomers of 1-phenylsulfonyl-1-acetyl-2-vinylcylopropane

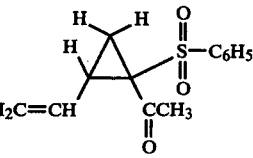

were obtained upon further workup of the crude material and employing a Waters Preparatory Liquid Chromatograph 500 A equipped with a gel permeation column and operated at a flow rate of 0.1 l/min. trans-1-phenylsulfonyl-1-acetyl-2-vinylcyclopropane mass spectrum m/e 250(M+)

nmr (CDCl$_3$) τ 1.80–2.37(5 phenyl H, mult.); 4.20–4.75 (3 vinyl H, mult.); 6.60–7.75(1H(2 cyclopropyl ring position), b mult.); 7.60(3H(CH$_3$CO—),s.); 7.85–8.2(2H(3 cyclopropyl ring position), mult.). cis 1-phenylsulfonyl-1-acetyl-2-vinylcyclopropane mass spectrum m/e 250(M+)

nmr (CDCl$_3$) τ 1.80–2.45(5 phenyl H, mult.); 3.45–5.05 (3 vinyl H, br. vinyl pattern); 7.60(1H(2 cyclopropyl ring position), br. mult. centered at 7.50τ); 7.55(3H(CH$_3$CO—), s.); 8.00–9.15(2H(3 cyclopropyl ring position), well defined mult.).

When methylsulfonylacetone, α-methylsulfonylacetophenone, α-phenylsulfonylpinacolone, α-phenylsulfonylacetophenone and phenylsulfonylacetone are reacted with 1,4-dichlorobutene-2 or 1,4-dibromobutene-2 in a similar manner, the corresponding cyclopropyl sulfones and sulfoxide are obtained. All of these compounds polymerize under anionic or radical conditions.

We claim:

1. A compound of the formula

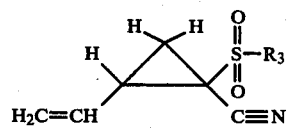

wherein R$_3$ is C$_{1-8}$ alkyl, C$_{3-8}$ alkenyl, cyclohexyl, phenyl, benzyl or C$_{1-4}$ alkyl-substituted cyclohexyl, phenyl or benzyl.

2. 1-Phenylsulfonyl-1-cyano-2-vinylcyclopropane.

* * * * *